United States Patent [19]

Gehrmann et al.

[11] 4,101,573
[45] Jul. 18, 1978

[54] PRODUCTION OF METHYLDICHLOROPHOSPHANE

[75] Inventors: Klaus Gehrmann; Alexander Ohorodnik, both of Erftstadt; Karl-Heinz Steil, Hürth; Stefan Schäfer, Brühl, all of Fed. Rep. of Germany

[73] Assignee: Hoechst Aktiengesellschaft, Frankfurt am Main, Fed. Rep. of Germany

[21] Appl. No.: 809,619

[22] Filed: Jun. 24, 1977

[30] Foreign Application Priority Data

Jun. 30, 1976 [DE] Fed. Rep. of Germany ....... 2629299
Jan. 14, 1977 [DE] Fed. Rep. of Germany ....... 2701389

[51] Int. Cl.² .............................. C07F 9/02; C07F 9/52
[52] U.S. Cl. .................................................. 260/543 P
[58] Field of Search ..................................... 260/543 P

[56] References Cited

U.S. PATENT DOCUMENTS 3,210,418  10/1965  Pianfetti ........................... 260/543 P

FOREIGN PATENT DOCUMENTS 2,046,314  5/1976  Fed. Rep. of Germany.
7,013,363  3/1972  Netherlands.

OTHER PUBLICATIONS

Pianfetti et al., J. Am. Chem. Soc., vol. 84, pp. 851-854, (1962).

*Primary Examiner*—Gerald A. Schwartz
*Attorney, Agent, or Firm*—Connolly and Hutz

[57] ABSTRACT

Methyldichlorophosphane is made by reacting methane with phosphorus trichloride in contact with carbon tetrachloride at temperatures higher than 500° C. To this end, the starting reactant mixture is admixed with 2 to 7 mol % of reaction-initiating carbon tetrachloride, based on phosphorus trichloride; the carbon tetrachloride is reacted to an extent of 50 to 80% by varying the reaction temperature within the range 550° to 650° C for constant residence times of 0.1 to 0.9 second; and resulting reaction mixture containing a residual analytically detectable 20 to 50% proportion of the carbon tetrachloride used is condensed out.

3 Claims, No Drawings

PRODUCTION OF METHYLDICHLOROPHOSPHANE

The preparation of dichlorophosphanes has been reported in Houben-Weyl, Methoden der Organischen Chemie, vol. 12/1, pages 302-316 (1963). The dichlorophosphanes belong to a class of compounds which are meanwhile widely used not only in preparative chemistry but also, to an increasing extent, in commercial operations, predominantly as starting materials for flameproofing fibers and plastics materials. The commercially most interesting representative of the above compounds is methyldichlorophosphane of the formula $H_3C-PCl_2$, last but not least in view of the fact that the first member compound of the alkyldichlorophosphanes contains a maximum of phosphorus which critically determines their use in flame-proofing fibers and plastics materials.

Various processes for making methyldichlorophosphane have already been described. Of special interest is the reaction of $PCl_3$ with methane at temperatures higher than 500° C at which the formation of methyldichlorophosphane tends to be favored under the particular thermodynamic conditions prevailing.

The preparation of methyldichlorophosphane has more fully been described in an article by J. A. PIANFETTI and L. D. QUIN in J. Am. Chem. Soc. 84 (1962), pages 851-854. As described in this literature reference, the reaction of methane and $PCl_3$, even if carried out at temperatures higher than 500° C, produces methyldichlorophosphane in poor yields which, however, can be improved by the addition of a catalyst, such as oxygen, for example.

The catalysts used in the process disclosed in U.S. Patent Specification No. 3 210 418 include oxygen, chlorine and nitrogen oxides which, however, produce the adverse effects described in German Patent Specification "Auslegeschrift" 2 046 314. More specifically, solid residues tend to be formed by the addition of chlorine, whereas corrosive by-products, such as alkyl phosphonic acid dichlorides and phosphorus oxyhalides, are obtained in all those cases in which oxygen is used as the catalyst. As shown in Example 7 of U.S. Patent Specification No. 3 210 418, the $PCl_3$-conversion rate is 16% and the methyldichlorophosphane yield is 90%, based on the $PCl_3$ which undergoes conversion. The U.S. Patent does, however, not exemplify the catalytic behaviour of nitrogen oxides.

A further process for making methyldichlorophosphane has been disclosed in German Patent Specification "Auslegeschrift" No. 2 046 314, wherein $PCl_3$ is reacted with one or more lower alkanes in the presence of phosgene at temperatures between 350° and 750° C, Example 4 illustrating the reaction of methane with $PCl_3$ in the presence of 0.6 mol % of phosgene at 625° C. As it would appear from the numerical values in that Example, methyldichlorophosphane is obtained in a yield of about 1%, based on the $PCl_3$ used. In other words, in all those cases in which the reaction of methane with $PCl_3$ is catalyzed by means of phosgene, it is just possible to avoid the formation of solid residues and corrosive by-products. With the fact in mind that the formation of by-products greatly depends on the $PCl_3$-conversion rate, it is obvious that less by-product is obtained at the price of a lower $PCl_3$-conversion rate.

U.S. Patent Specification No. 3 519 685, Example 5, describes reacting methane with $PCl_3$ at 545° to 555° C with the use of carbon tetrachloride as a catalyst. The resulting reaction product contains about 7% of methyldichlorophosphane.

A still further process for making aliphatic dihalogenophosphanes has been described in Dutch Patent Specification 7 013 363, wherein a halogenated hydrocarbon, e.g. $CCl_4$, is used as a catalyst. All the working Examples in that Patent relate exclusively to the preparation of ethyldichlorophosphane from ethane and $PCl_3$. The catalyst is used in proportions of 3 to 20 mol %, based on $PCl_3$. Alkane and $PCl_3$ are used in preferred molar ratios of 3 : 1 to 5 : 1. The reaction temperatures are between 450° to 650° C and the reaction mixture is allowed to remain in the reaction zone for a period of 1 to 20, preferably 5 to 10 seconds. As more specifically described in Example 1 of Dutch Patent Specification 7 013 363, wherein the material is reacted at 540° C, allowed to remain in the reaction zone for a period of 7 seconds and used in admixture with 8.9 mol % of catalyst, based on $PCl_3$, the $PCl_3$-conversion rate is 37%, the ethyldichlorophosphane yield is 82%, based on the $PCl_3$ used, and the $CCl_4$-conversion rate is 90%. This admittely good result is obtainable only in connection with the preparation of ethyldichlorophosphane. With respect to the preparation of methyldichlorophosphane by the process described in Dutch Patent Specification No. 7 013 363, it should, however, not be ignored that methyldichlorophosphane is very liable to undergo decomposition which has adverse effects on the primary yield downstream of the reactor. In addition to this, as a result of the unfavorable difference between the boiling points of the respective materials (carbon tetrachloride: 76.7° C; methyldichlorophosphane: 81.6° C; ethyldichlorophosphane: 113° C) considerably more material would be lost on separating $CCl_4$ distillatively from methyldichlorophosphane than from ethyldichlorophosphane.

In view of the fact that the bulk of carbon tetrachloride itself undergoes conversion, the reference to $CCl_4$ as a catalyst is certainly not correct. The $CCl_4$ undergoes decomposition whereby the reaction of methane with $PCl_3$ is initiated not really catalyzed, and for this reason reference is made in the present invention to $CCl_4$ as a reaction initiator or starter.

In an attempt to provide a technically satisfactory process for making methyldichlorophosphane, we have now unexpectedly found that carbon tetrachloride is capable of initiating not only the formation of methyldichlorophosphane at temperatures higher than 500° C in accordance with the following equation:

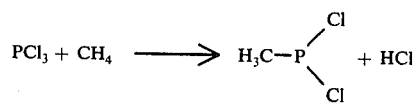

but also its decomposition at boiling temperature in accordance with the following equations:

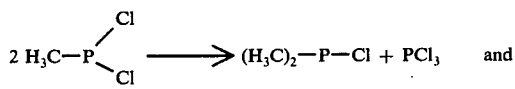

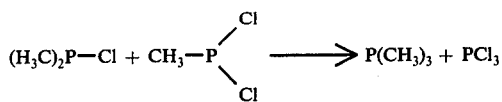

Both dimethylchlorophosphane and trimethylphosphane together with hydrogen chloride, which is always contained in the reaction medium, form highly undesirable salts which contaminate the reactor and in addition to this are highly corrosive.

The CCl$_4$-initiated decomposition of methyldichlorophosphane occurs at reaction temperatures of 500° to 600° C and residence times of the reaction material in the reaction zone of less than 1 second, as well as at lower temperatures (boiling point of reaction mixture: approximately 75° C) and longer residence times of $10^1$ second and more. This is the explanation why the CCl$_4$-initiated reaction of methane with PCl$_3$ has to be effected with minor quantities of initiator and why the conversion rates remain low. If initiated with more starter, the reaction gives higher conversion rates but lower yields.

Despite these unfavorable facts, we have found that it is possible by means of a CCl$_4$-initiated reaction of methane with PCl$_3$ to produce methyldichlorophosphane in very good yields, with satisfactory conversion rates under commercially attractive conditions.

The present invention relates mor particularly to a process for making methyldichlorophosphane by reacting methane with phosphorus trichloride in contact with carbon tetrachloride at temperatures higher than 500° C, which comprises: admixing the starting reactant mixture with 2 to 7 mol % of reaction-initiating carbon tetrachloride, based on phosphorus trichloride; reacting the carbon tetrachloride to an extent of 50 to 80% by varying the reaction temperature within the range 550° to 650° C for constant residence times of 0.1 to 0.9 second; and condensing out the resulting reaction mixture containing a residual analytically detectable 20 to 50% proportion of the carbon tetrachloride used.

Preferred features of the present process provide:

a. for the starting reactant mixture to be admixed with 3 to 5 mol % of reaction-initiating carbon tetrachloride, based on phosphorus trichloride, and b. for a constant residence time of 0.3 to 0.8 second to be used.

Under the conditions described, the methane undergoes reaction with PCl$_3$ to give methyldichlorosphosphane, which is obtained in a yield of 92 to 99%, based on the PCl$_3$ which undergoes conversion at a rate of 15 to 32%.

The reaction to methyldichlorophosphane in accordance with the equation:

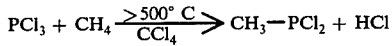

is critically determined by the reaction temperature, initiator (CCl$_4$) concentration, and residence time. It is not, however, possible to increase the degree of reaction at will inasmuch as the formation of undesirable solid material tends to be favored at increasing conversion rates.

In accordance with our present invention we have additionally found that an identical conversion rate to methyldichlorophosphane can be obtained for identical residence times and initiator concentration but at lower temperatures, i.e. at temperatures lower than 550° C but higher than 500° C, more specifically at temperatures within the range 500° to 550° C, by carrying out the reaction in an elongated reactor, namely at higher flow velocities, e.g. of 25 to 100 m per second. In this event considerably less undesirable solid material is obtained than at lower flow velocities of 1 to less than 25 m per second, i.e. in short reactors.

In other words the statements made herein can be summarized to the effect that the reaction temperature may be varied in accordance with this invention within the limits of 500° to 650° C. This temperature range corresponds to flow velocities of 1 to 100 m per second.

In marked contrast with an O$_2$-catalyzed process, the CCl$_4$-initiated reaction of the present invention remains substantially free from by-products which impair the yield of desirable product. As it would appear from the nature and quantity of by-products detected in the reaction mixture, the reaction is initiated by chlorine radicals which originate from the carbon tetrachloride molecule.

Inasmuch as the reaction mixture has been found to contain chloroform, hexachloroethane, tetrachloroethylene in proportions corresponding to the quantity of carbon tetrachloride used, but considerably less great proportions of vinylidene chloride, the CCl$_4$-initiator may reasonably be assumed to react chiefly with itself, to some minor extent with methane but not demonstrably with the phosphorus compounds present in the reaction mixture. The phosphorus compounds may be classified as being the most valuable material and carbon tetrachloride as the least valuable material with methane lying therebetween. This is determinative of a further desirable aspect of the present process.

In order to make it possible for the reaction of PCl$_3$ with methane to methyldichlorophosphane to proceed under optimum conditions, it is necessary for a certain quantity of chlorine radicals to be available per unit time. If the concentration of radicals is too high, by-products tend to be formed at an increasing rate, while too low a concentration of such radicals adversely affects the PCl$_3$-conversion rate. The concentration of active chlorine radicals does, however, not solely depend on the concentration of the tetrachloride used. It also depends on the temperature and residence time.

In combining the various steps of the present invention, it is good practice to admix PCl$_3$ with a constant quantity of CCl$_4$, e.g. 5 mol %. The constant supply of material results in a constant residence time so that it is possible to establish an optimum concentration of radicals just by regulating the temperature prevailing in the reaction zone by means of the CCl$_4$-conversion rate.

If it is desirable for the conversion rate to be increased or for the residence time to be shortened for an identical composition of the starting reactants, it is additionally possible to increase the reaction temperature via the carbon tetrachloride conversion rate and in this manner to provide the optimum concentration of radicals and hence the optimum reaction conditions. This method of controlling the optimum reaction conditions is only applicable to the narrow range of disclosed in this invention.

The molar ratio of methane to $PCl_3$ does not form part of the invention. It may however be varied as desired within the limits of 10 : 1 to 1 : 1.

EXAMPLES 1 to 13:

An electrically heatable stainless tube ("Hastelloy C"-tube) which was 180 cm long and had a free reactor volume of 778 cc was charged with gaseous mixtures of methane and $PCl_3$ in the molar ratio of 4 : 1, while varying in each particular case the quantity of $CCl_4$-initiator, residence time and reaction temperature. The reaction mixture coming from the reactor was cooled stagewise down to $-60°$ C and the resulting condensate was subjected to gas chromatography.

| Ex. No. | $CCl_4$ (mol %) | Residence time (s) | React. temp. (° C) | $CCl_4$- conversion rate (mol %) | $PCl_3$- conversion rate (mol %) | MDP** yield (%) |
|---|---|---|---|---|---|---|
| 1 | 0 | 0.8 | 590 | — | 4 | 80 |
| 2 | 3 | 0.8 | 580 | 68 | 15 | 98.5 |
| 3 | 3 | 0.8 | 590 | 70 | 16 | 98 |
| 4 | 5 | 0.8 | 580 | 65 | 18 | 98 |
| 5 | 5 | 0.8 | 590 | 69 | 23 | 96 |
| 6 | 5 | 0.5 | 600 | 70 | 24 | 95 |
| 7 | 5 | 0.3 | 610 | 70 | 23 | 96 |
| 8 | 5 | 0.8 | 610 | 78 | 28 | 95 |
| 9 | 5 | 0.5 | 580 | 60 | 12 | 98 |
| 10 | 7 | 0.8 | 590 | 63 | 30 | 94 |
| 11 | 7 | 0.5 | 600 | 65 | 32 | 92 |
| 12 | 8 | 0.8 | 580 | 55 | 32 | 87 |
| 13 | 10 | 0.8 | 580 | 50 | 34 | 85 |

*Mol %, based on $PCl_3$ used
**Methyldichlorophosphane yield, based on $PCl_3$ converted.

EXAMPLES 14 and 15:

An electrically heatable stainless tube (Hastelloy C) which was 20 m long and had a free reactor volume of 29 liter was charged with 96 normal m³ (S.T.P.) of methane and 126 kg of $PCl_3$ in vapor form which contained 5 mol % of carbon tetrachloride, based on $PCl_3$. The residence time was kept constant but the temperature was varied. The reaction mixture coming from the reactor was cooled stagewise down to $-60°$ C and the resulting condensate was subjected to gas chromatography.

| Ex. No. | React. temp. ° C | $CCl_4$- conversion rate mol % | $PCl_3$- conversion rate mol % | MDP-* yield % |
|---|---|---|---|---|
| 14 | 530 | 60 | 12 | 98.5 |
| 15 | 549 | 65 | 18 | 98.5 |

*Methyldichlorophosphane yield, based on $PCl_3$ converted.

Examples 1, 12 and 13 are comparative Examples, and Examples 2 to 11, 14 and 15 illustrate the invention.

We claim:

1. A process for making methyldichlorophosphane by reacting methane with phosphorus trichloride in contact with carbon tetrachloride at temperatures higher than 500° C which comprises: admixing the starting reactant mixture with 2 to 7 mol % of reaction-initiating carbon tetrachloride, based on phosphorus trichloride; reacting the carbon tetrachloride to an extent of 50 to 80% by varying the reaction temperature within the range 550° to 650° C for constant residence times of 0.1 to 0.9 second; and condensing out the resulting reaction mixture containing a residual analytically detectable 20 to 50% proportion of the carbon tetrachloride used.

2. The process as claimed in claim 1, wherein the starting reactant mixture is admixed with 3 to 5 mol % of reaction-initiating carbon tetrachloride, based on phosphorus trichloride.

3. The process as claimed in claim 1, wherein a constant residence time of 0.3 to 0.8 second is used.

* * * * *